(12) United States Patent
McCormick et al.

(10) Patent No.: US 11,298,498 B2
(45) Date of Patent: Apr. 12, 2022

(54) BREATHING SYSTEM FOR ANESTHESIA MACHINE

(71) Applicant: GE Precision Healthcare LLC, Wauwatosa, WI (US)

(72) Inventors: Timothy P. McCormick, Madison, WI (US); James N. Mashak, Sun Prairie, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 412 days.

(21) Appl. No.: 16/407,869

(22) Filed: May 9, 2019

(65) Prior Publication Data
US 2020/0353201 A1 Nov. 12, 2020

(51) Int. Cl.
| | | |
|---|---|---|
| *A61M 16/10* | (2006.01) | |
| *A61M 16/12* | (2006.01) | |
| *A61M 16/22* | (2006.01) | |
| *A61M 16/20* | (2006.01) | |

(52) U.S. Cl.
CPC ...... *A61M 16/104* (2013.01); *A61M 16/1045* (2013.01); *A61M 16/12* (2013.01); *A61M 16/208* (2013.01); *A61M 16/22* (2013.01); *A61M 2016/1025* (2013.01); *A61M 2205/121* (2013.01); *A61M 2205/125* (2013.01); *A61M 2205/7545* (2013.01)

(58) Field of Classification Search
CPC .............. A61M 16/00; A61M 16/0057; A61M 16/0078; A61M 16/0081; A61M 16/009; A61M 16/01; A61M 16/08; A61M 16/0883; A61M 16/0891; A61M 16/10; A61M 16/104; A61M 16/1055; A61M 16/1065; A61M 16/12; A61M 16/18; A61M 16/201; A61M 16/208; A61M 16/22; A61M 2016/0039; A61M 2016/0042
See application file for complete search history.

(56) References Cited

U.S. PATENT DOCUMENTS

| | | |
|---|---|---|
| 4,007,737 A | 2/1977 | Paluch |
| 4,051,847 A | 10/1977 | Henkin |
| (Continued) | | |

*Primary Examiner* — Joseph D. Boecker
(74) *Attorney, Agent, or Firm* — Andrus Intellectual Property Law, LLP (57) ABSTRACT

An anesthesia machine includes a gas mixer providing gas for delivery to a ventilated patient and a breathing system. The breathing system includes a reusable ventilation portion and a disposable circle portion. The reusable ventilation portion includes a mechanical ventilation section, a manual ventilation section, a ventilation port, and switch configured to switch between connection of the mechanical ventilation section and the manual ventilation section to drive patient ventilation. The disposable circle portion includes a vent connector that connects to the ventilation port, an inspiratory channel, and a gas intake port providing anesthetic gas from the gas mixer to the inspiratory channel. The disposable circle portion further includes an expiratory channel, a $CO_2$ absorber, and a filter positioned in a flow path between the expiratory port and the vent connector and between the $CO_2$ absorber and the vent connector. The filter is configured to prevent moisture and bacteria from entering the reusable ventilation portion of the breathing system.

20 Claims, 5 Drawing Sheets

(56) References Cited

U.S. PATENT DOCUMENTS

| | | | |
|---|---|---|---|
| 4,791,922 A * | 12/1988 | Lindsay-Scott ... | A61M 16/0081 128/205.28 |
| 4,883,051 A | 11/1989 | Westenskow et al. | |
| 4,991,576 A * | 2/1991 | Henkin ................. | A61M 16/00 128/203.28 |
| 5,320,093 A * | 6/1994 | Raemer ............... | A61M 16/085 128/203.12 |
| 6,131,571 A * | 10/2000 | Lampotang ....... | A61M 16/0009 128/204.21 |
| 2007/0051367 A1* | 3/2007 | Mashak ................ | A61M 16/22 128/203.12 |
| 2010/0037896 A1* | 2/2010 | Mashak ............ | A61M 16/0078 128/205.12 |
| 2013/0061849 A1* | 3/2013 | Lemper ................ | A61M 16/20 128/200.16 |
| 2014/0005566 A1* | 1/2014 | Homuth ............ | A61M 16/0078 600/538 |
| 2014/0261416 A1* | 9/2014 | Arcilla ................ | A61M 16/107 128/203.14 |

\* cited by examiner

BREATHING SYSTEM FOR ANESTHESIA MACHINE

BACKGROUND

The present disclosure generally relates to anesthesia machines comprising breathing systems, and more particularly to a breathing system for an anesthesia machine having a disposable portion and a reusable portion.

Conventional anesthesia machines comprise breathing systems that deliver breathing gases to the patient comprising oxygen and other gases, optionally infused with an inhalational anesthetic agent. As used herein, the term "ventilation" refers to a process of providing mechanical assistance to a patient for breathing. As used herein, "inspiratory gases" refers to gases transported along an inspiratory channel of the patient delivery circuit, including gases that are inhaled or inspired by a patient and gases bypassing patient inhalation and transported directly into an expiratory channel of the patient delivery circuit. Also, as used herein, "expiratory gases" refer to gases that are exhaled or expired by the patient into the expiratory channel of the patient delivery circuit and gases transported directly into the expiratory channel from the inspiratory channel which are not exhaled by the patient, both of which are transported along the expiratory channel. Conventional breathing systems typically include a mechanical ventilation drive, such as bellows systems where patient ventilation is driven by a bellow, and a manual ventilation drive, such as a bag.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, an anesthesia machine includes a gas mixer that provides an anesthetic gas for delivery to a ventilated patient and a breathing system. The breathing system includes a reusable ventilation portion and a disposable circle portion. The reusable ventilation portion includes a mechanical ventilation section, a manual ventilation section, a ventilation port, and switch configured to switch between connection of the mechanical ventilation section and the manual ventilation section to drive patient ventilation through the ventilation port. The disposable circle portion includes a vent connector that connects to the ventilation port, an inspiratory channel having an inspiratory port that connects to a patient connector and delivers inspiratory gasses thereto, and a gas intake port providing anesthetic gas from the gas mixer to the inspiratory channel. The disposable circle portion further includes an expiratory channel having an expiratory port that connects to the patient connector and receives expiratory gasses therefrom, a $CO_2$ absorber, and a filter positioned in a flow path between the expiratory port and the vent connector and between the $CO_2$ absorber and the vent connector. The filter is configured and positioned to prevent moisture and bacteria from entering the reusable ventilation portion of the breathing system.

One embodiment of a removable breathing system for an anesthesia machine includes a reusable ventilation portion and a disposable circle portion. The reusable ventilation portion includes a mechanical ventilation section, a manual ventilation section, a ventilation port, and a switch configured to switch between connection of the mechanical ventilation section and connection of the manual ventilation section to drive patient ventilation through the ventilation port. The disposable circle portion is removably connected to the reusable ventilation portion and includes a vent connector that connects to the ventilation port, an inspiratory channel terminating at an inspiratory port that connects to a patient connector and delivers inspiratory gasses thereto, and a gas intake port providing anesthetic gas from the gas mixer to the inspiratory channel. The disposable circle portion further includes an expiratory channel terminating at an expiratory port that connects to the patient connector and receives expiratory gasses therefrom. The disposable circle portion may further include a $CO_2$ absorber connecting between the expiratory channel and inspiratory channel. The disposable circle portion includes a filter positioned in a flow path of the expiratory gasses between the expiratory port and the vent connector, wherein the filter prevents moisture and bacteria and the expiratory gasses from entering the reusable ventilation portion of the breathing system. The filter may also be positioned and configured in a flow path between the $CO_2$ absorber and the vent connector to thereby absorb and prevent moisture generated by the $CO_2$ absorber from entering the reusable ventilation portion of the breathing system.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Breathing systems of anesthesia machines typically require cleaning and disinfection or sterilization between cases to minimize cross contamination between patients. This is a costly and time consuming process and requires significant management and verification by a healthcare facility to verify and document proper execution of the complex cleaning process. The inventors have recognized a need for simplifying the cleaning and disinfection or sterilization process for anesthesia machines. Moreover, the inventors have recognized that mold and bacteria growth problems exist with current breathing systems where mold and bacteria growth occurs in the gas flow path that reaches the patient. For example, water vapor is produced as a result of the chemical reaction of the $CO_2$ absorber, and moisture is present in the breathing gases exhaled by the patient. This moisture may collect in the inspiratory channel of the breathing circuit, for example, or in other parts of the breathing system. Such moisture provides an environment that fosters mold and bacterial growth. Accordingly, the inventors have also recognized a need to limit the possibility of mold growth within the breathing system.

In view of the foregoing problems and challenges in the relevant art, the inventors developed the disclosed breathing system, which includes a disposable circle portion that removably connects to a reusable ventilation portion. The disposable portion of the breathing system interacts with the expiratory gasses from the patient and prevents moisture and bacteria and expiratory gasses from entering the reusable ventilation portion. Specifically, the disposable portion includes a filter positioned in a flow path of the expiratory gasses. The filter prevents moisture and bacteria from entering the reusable portion of the breathing system. For example, the filter may be a heat and moisture exchange filter (HMEF). Alternatively, the filter may be a high efficiency particulate air (HEPA) filter. For example, the disposable portion of the breathing system is configured for use with only a single patient. Thereby, the reusable ventilation portion does not need to be cleaned and/or disinfected between each patient use, and the disposable portion of the breathing system gets replaced after each patient use. As disclosed herein, replacement of the disposable circle portion of the breathing system is much simpler than the complex cleaning and disinfection or sterilization process.

Figure 1:
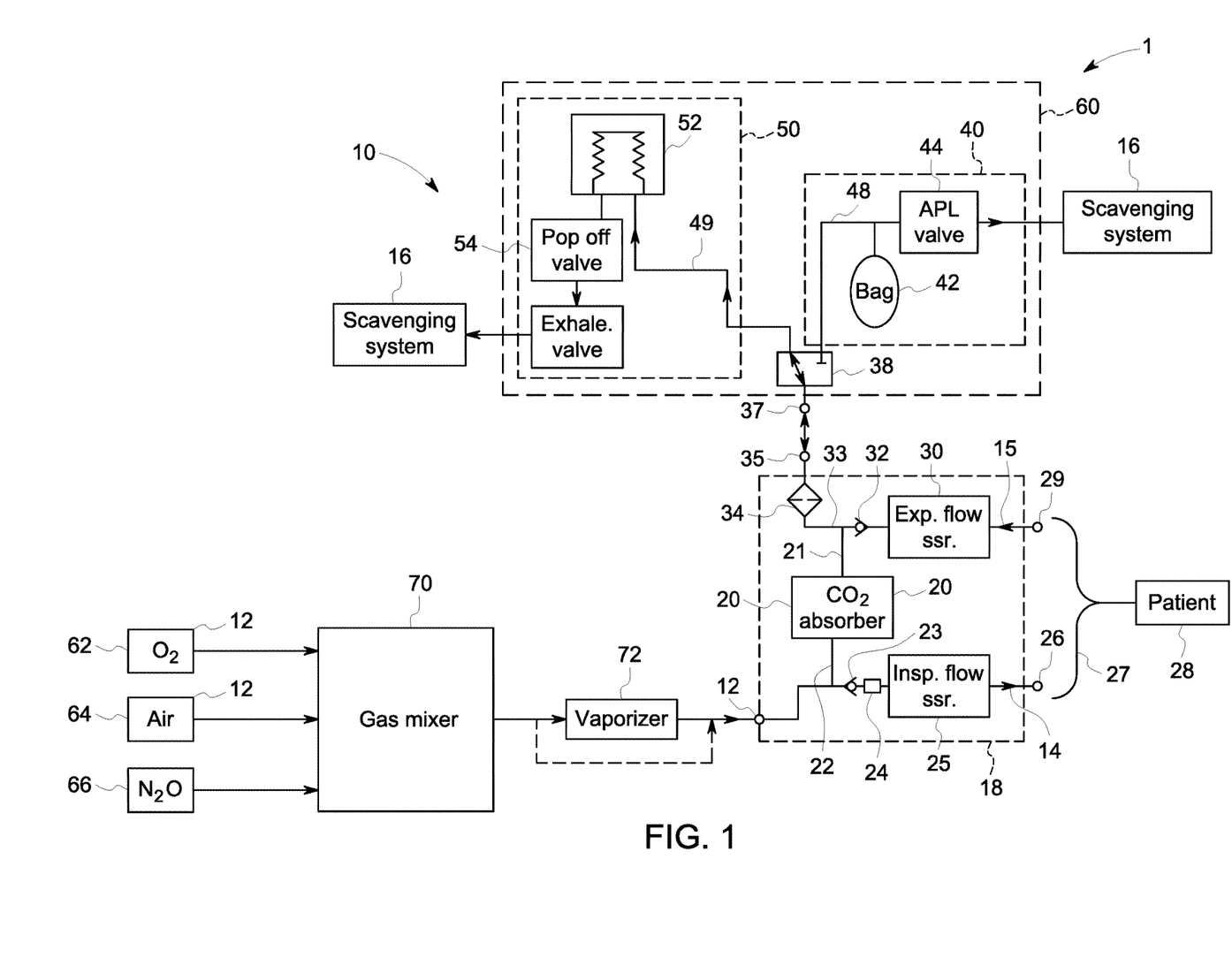
FIG. 1 is a system diagram of an exemplary anesthesia machine and breathing system according to one embodiment of the present disclosure.
Figure 2:
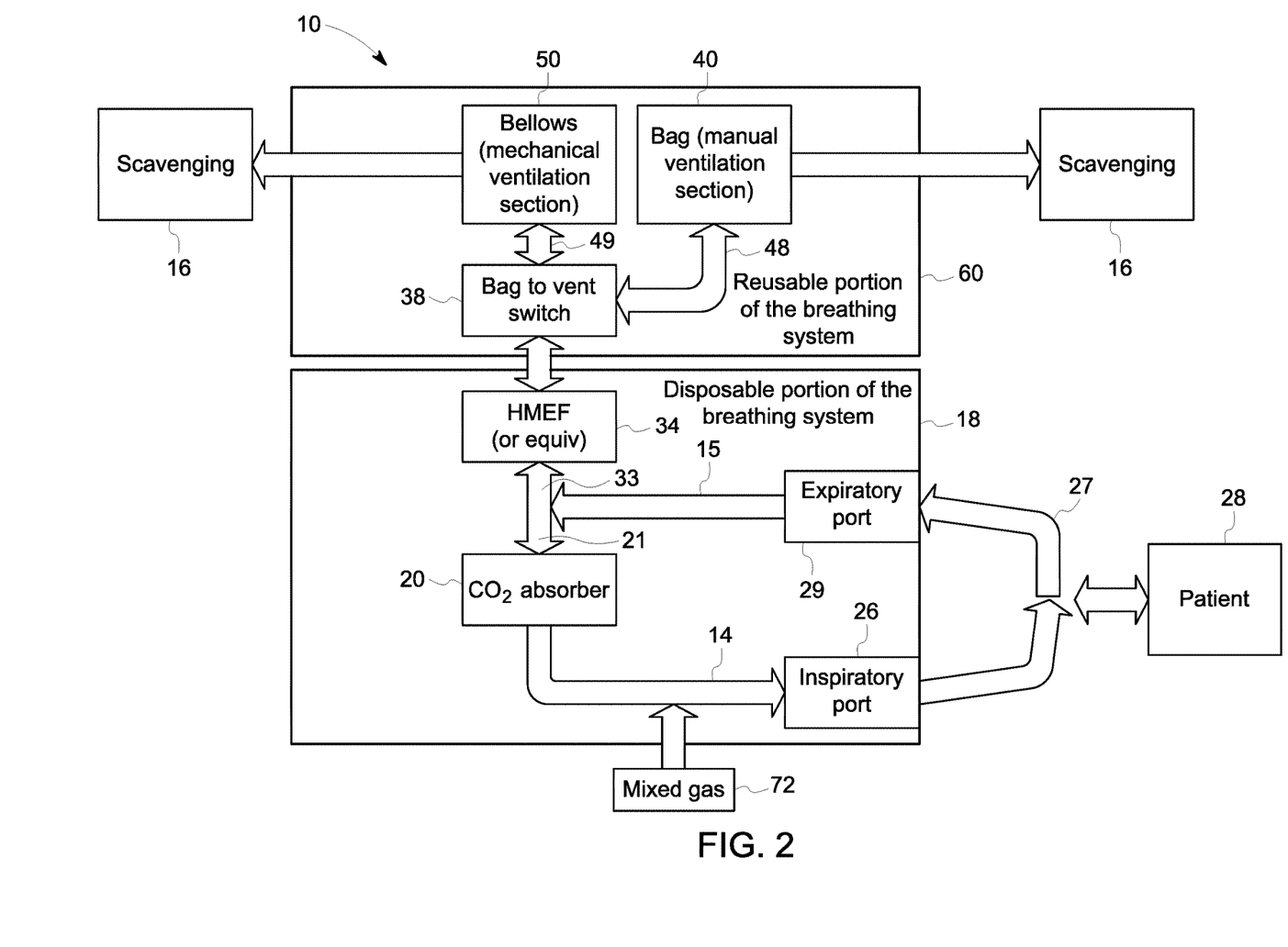
FIG. 2 is a system diagram of a breathing system according to an embodiment of the present disclosure.

FIG. 1 depicts one embodiment of an anesthesia machine 1 that includes a gas mixer 70, a breathing system 10 and a scavenging system 16. The breathing system includes a circle portion 18, or patient delivery circuit, and a ventilation portion 60. The circle portion 18 is disposable and is removably connectable to the ventilation portion 60, which is reusable. The ventilation portion 60 includes a manual ventilation section 40 and a mechanical ventilation section 50. FIG. 2 also provides a simplified diagram of a breathing system, including a reusable ventilation portion 60 and a disposable circle portion 18.

During patient ventilation, input gas flows from a gas mixer 70 that mixes several gas sources, such as from an $O_2$ source 62, a medical air source 64, and/or a nitrous oxide ($N_2O$) source 66. In the example, the output of the gas mixer 70 is provided to the vaporizer 72 that provides vaporized anesthetic agent into the gas to be delivered to the patient. In certain embodiments, a bypass channel may also be provided that allows gases to bypass the vaporizer on the path to the patient 28. Gas then flows to the breathing system, entering the gas inlet port 12. Gas flows through the inspiratory channel 14 of the disposable circle portion 18, including through the one-way valve 23, the $O_2$ sensor 24, the inspiratory flow sensor 25 and to the inspiratory port 26. The inspiratory port 26 connects to a patient-end connector 27. The patient connector 27 may be, for example, a wye tube that connects to a patient interface, such as a mask or endotracheal tube, in order to delivery and receive breathing gasses for the patient 28.

During ventilation, expiratory gasses from the patient 28 travel through the patient connector 27 to the expiratory port 29 of the disposable circle portion 18. The expiratory gasses travel through the expiratory channel 15, including past the flow sensor 30 and the one-way expiratory valve 32. The expiratory channel 15 and the $CO_2$ absorber inlet channel 21 connect at a common channel 33. The $CO_2$ absorber 20 connects between the expiratory channel 15 and the inspiratory channel 14 and removes $CO_2$ from gasses prior to reaching the inspiratory channel 14. The gas flows into the $CO_2$ absorber via the $CO_2$ inlet 21, through the $CO_2$ absorber 20 where $CO_2$ is removed therefrom, and the scrubbed gasses are provided to the $CO_2$ absorber outlet 22 to the inspiratory valve 23 and into the inspiratory channel 14.

In the embodiments at FIGS. 1 and 2, filter 34 is positioned in the common channel 33 and is configured to prevent moisture and bacteria in the expiratory gasses from entering the reusable ventilation portion 60. For example, the filter may be an HMEF or a HEPA filter. Thereby, bacteria and viruses present in the expiratory gasses are filtered out before exiting the disposable circle portion 18 and are kept out of the reusable portion of the breathing system 10. The filter 34 is positioned in the flow path of the expiratory gasses. In certain embodiments, the filter is also positioned in the flow path of inspiratory gasses between the vent connector 35 and the $CO_2$ absorber 20 such that gas is headed toward the inspiratory channel 14 also flow through the filter 34. Thus, the moisture generated by the $CO_2$ absorber is prevented from reaching the reusable portion 60. In FIGS. 1 and 2, the filter 34 is depicted as positioned in the common channel 33. In other embodiments, the filter 34 may be integrated into the vent connector 35, or may be positioned adjacent to the vent connector in the common channel 33. In still other embodiments, the filter 34 may be positioned elsewhere and/or more than one filter 34 may be utilized. For example, one filter may be positioned in the expiratory channel 15 or between the expiratory valve 32 and the location where the $CO_2$ absorber inlet channel 21 meets the common channel 33. Alternatively or additionally, a filter 34 may be positioned in $CO_2$ absorber inlet channel 21.

The disposable circle portion 18 removably connects to the reusable ventilation portion 60 such that the vent connector 35 connects to the ventilation port 37 on the reusable ventilation portion 60. A switch 38 is adjacent to the ventilation port 37 on the gas path and is configured to switch between connection of the mechanical ventilation section and the manual ventilation section to drive patient ventilation. The switch 38 may be, for example, a bag-to-vent switch as is common in existing breathing systems. The switch 38 occupies either of two positions such that it directs flow into either the manual ventilation section 40 or the mechanical ventilation section 50. Thus, the switch 38 is configured to be in either of two positions such that gas flow is directed into either a bag channel 48 or a ventilator channel 49, but not both.

During patient ventilation, the switch 38 opens only one drive channel at a time and does not permit both the bag channel 48 and the ventilator channel 49 to be opened simultaneously. In a bag position, the switch 38 opens the bag channel 48 and closes the ventilator channel 49. In a ventilator position, the switch 38 opens the ventilator channel 49 and closes the bag channel 48. In the bag position, the switch 38 directs gas into the bag channel 48 and through the manual ventilation section 40 where ventilation is driven by the bag 42 operating in conjunction with APL valve 44 to provide manual control of the patient ventilation. In the vent position, the switch 38 directs gas into the ventilation channel 49 and the mechanical ventilation section 50 where ventilation is driven by the bellows 52 and passes through the popup valve 54 and the exhalation valve 56.

In existing breathing systems, the ventilation drive sections are exposed to exhalation gasses from the patient as the gasses get cycled through the various drive portions. However, in the disclosed system, contaminants and moisture are kept out of the reusable ventilation portion 60. Namely, the gasses are filtered prior to entering the reusable ventilation portion 60. The filter 34 is either positioned in the disposable circle portion 18 or at the connection between the vent connector 35 and the ventilation port 37 and, at either location, removes bacteria, viruses, and moisture from the gasses exiting the circle portion 18 and entering the ventilation portion 60.

Figure 3A:
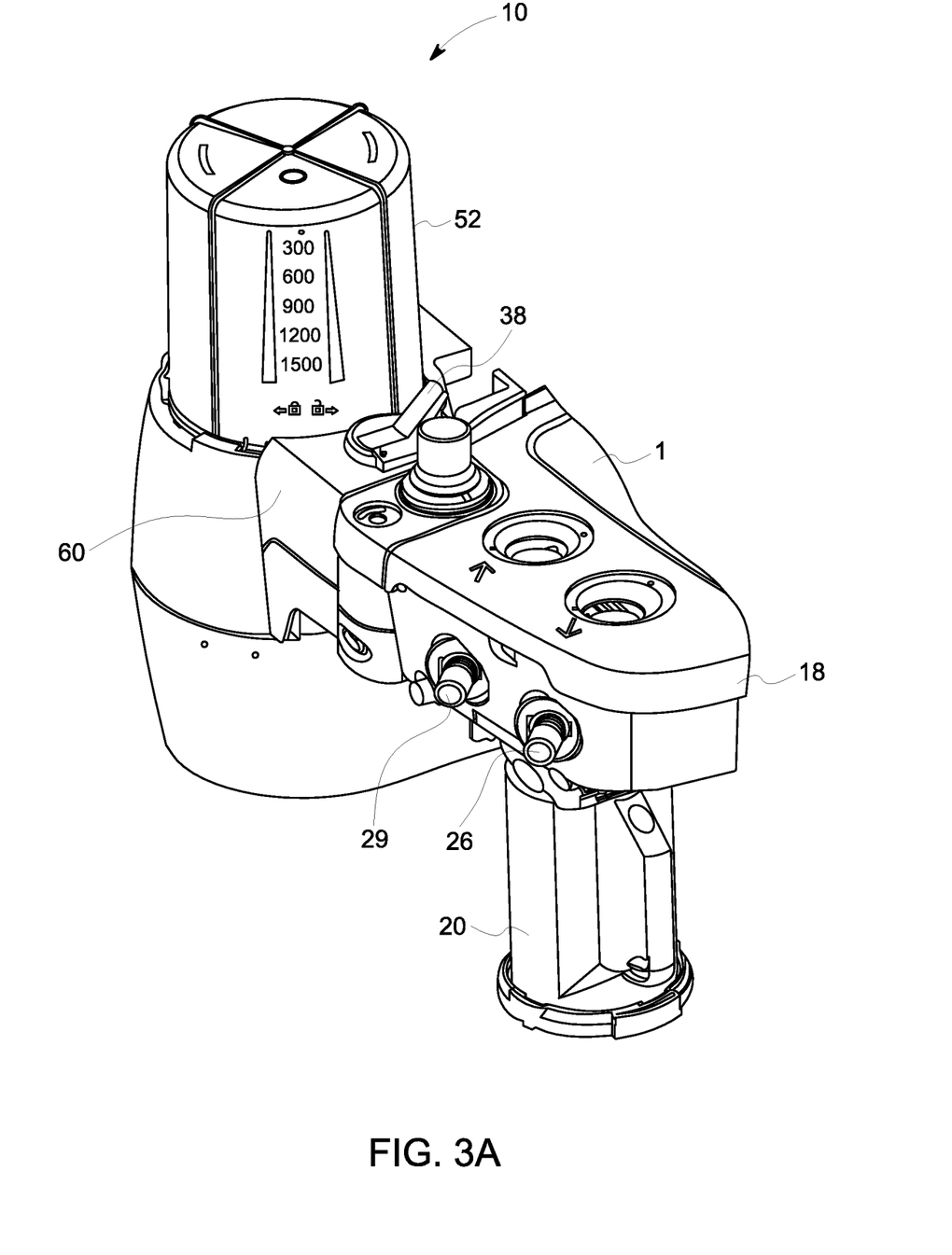
FIGS. 3A-3C depict another embodiment of a breathing system according to another embodiment of the present disclosure.
Figure 3B:
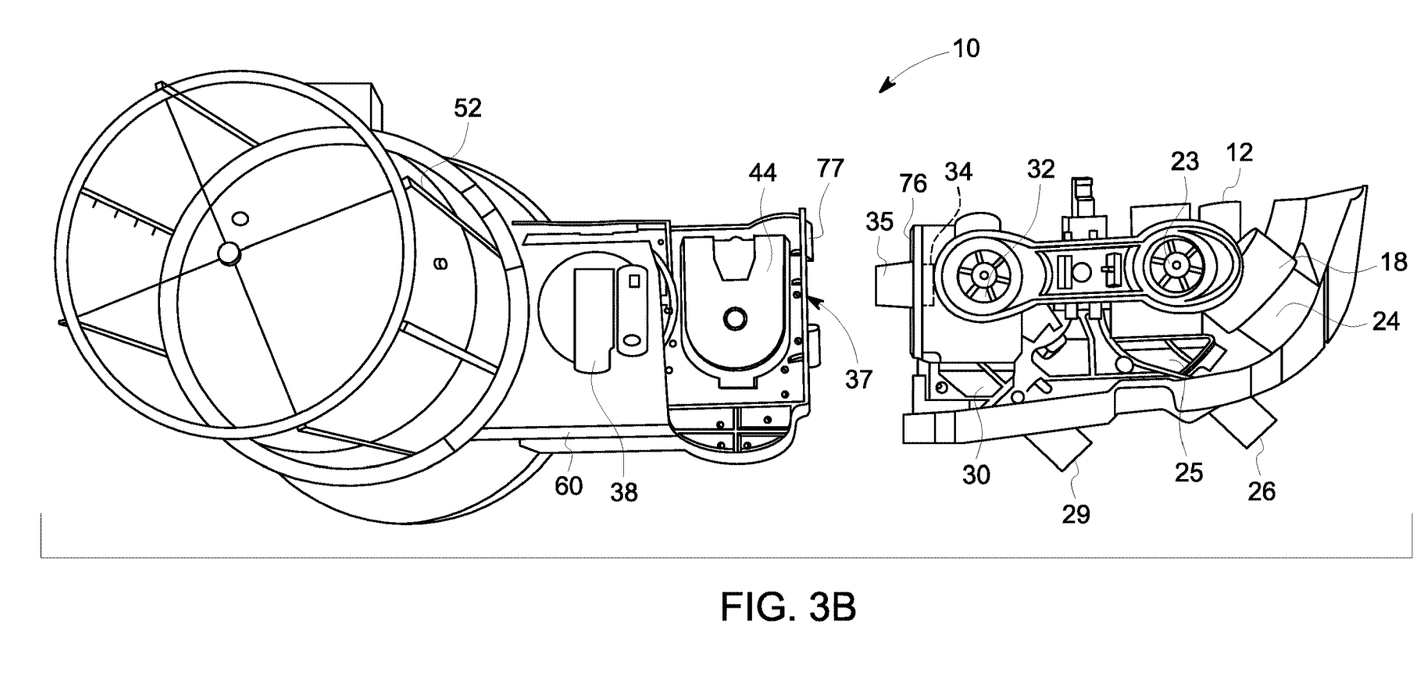
Figure 3C:
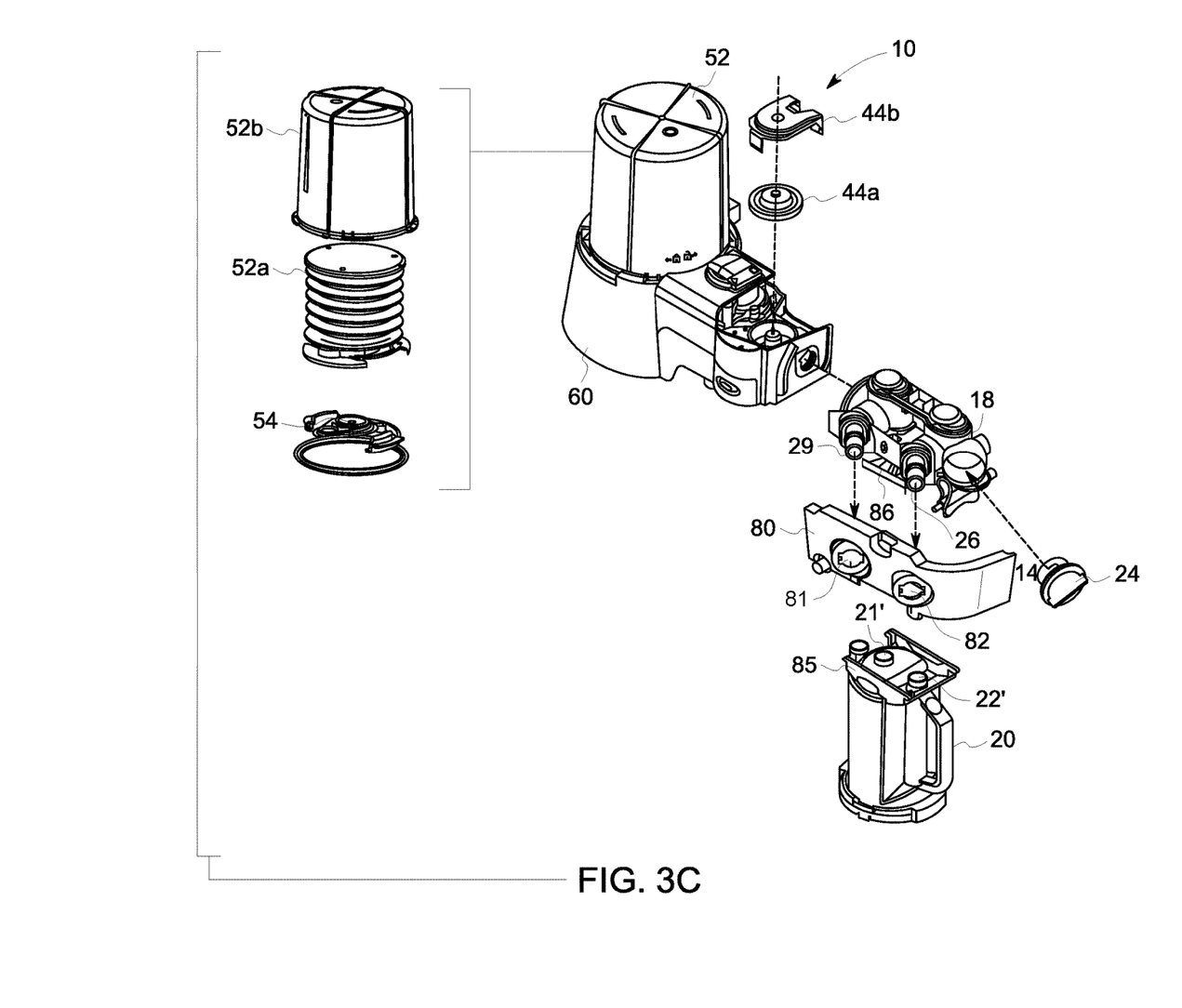

FIG. 3A depicts one embodiment of a breathing system 10 assembled on an anesthesia machine 1. FIGS. 3B and 3C depict embodiments of the breathing system 10 removed from the anesthesia machine 1. As shown in FIG. 3B, the breathing system 10 assembled to the anesthesia machine 1 provides exposed inspiratory port 26 and expiratory port 29 to which a patient connector, such as a wye piece gets attached. Movement of the switch 38 controls the ventilation drive means between the mechanical ventilation and manual ventilation drive sections, as described above. The breathing system 10 may be removable from the anesthesia machine 1 in a single piece, whereby the ventilation portion 60 and the circle portion 18 are attached to one another and removable as a unit. In other embodiments, the reusable ventilation portion 60 and the disposable circle portion 18 may each separately attach to the anesthesia machine 1, and may be maintained in an assembled connection by their respective attachments to the anesthesia machine 1.

FIG. 3B depicts an embodiment of the breathing system 10 where the disposable circle portion 18 is detached from the reusable ventilation portion 60. Respective attachment means are provided on each portion 18, 60 in order to attach them together. In the depicted embodiment, the circle portion 18 comprises a fitting 76 configured to mate with a reciprocal fitting 77 on the ventilation portion 60 so as to fasten the circle portion 18 to the ventilation portion 60 so that the breathing system 10 is connectable and disconnectable from the anesthesia machine 1 as a unit. In various embodiments, the fittings 76 and 77 may be any type of mechanical connections means or arrangement capable of connecting the two portions 18 and 60. For example, the fittings 76 and 77 may be a threaded connection, a friction fit, a hook and clasp, a bayonet, etc.

When the circle portion 18 is assembled to the ventilator portion 60, the vent connector 35 connects with the ventilation port 37 so as to provide a continuous channel for gas flow to flow between the two portions 18, 60. The filter 34 is positioned inside the circle portion 18 adjacent to the vent connector 35 so as to remove moisture and bacteria from gasses traveling out of the circle portion 18 and into the ventilation portion 60. Thereby, moisture migration is minimized and the ventilation portion 60 remains dry so as to avoid bacterial and mold growth. The circle portion 18 further includes the inspiratory valve 23, which is a one-way valve permitting inspiratory flow toward the inspiratory port 26, and expiratory valve 32 which is a one-way valve permitting flow of expiratory gasses from the expiratory port 29 to the common channel 33. The disposable circle portion 18 may further include an inspiratory flow sensor 25 and an expiratory flow sensor 30 incorporated therein. In other embodiments, the sensor portion may be removable from the disposable circle portion 18 and may be reusable. For example, the sensor portion may be autoclavable or otherwise sterilizable. Thus, upon replacement of the disposable circle portion 18, the sterilized sensor portion can be attached thereto prior to assembly to the anesthesia machine 1.

In various embodiments, the circle portion 18 may include an $O_2$ sensor 24 to measure oxygen in the inspiratory path. The $O_2$ sensor 24 may be integrated into the disposable circle portion 18, and thus may be configured for single use. In other embodiments, the $O_2$ sensor 24 may be removable and reusable. As shown in FIG. 3C, the $O_2$ sensor 24 may be removed from the disposable circle portion 18 and may be sterilizable and reusable. In other embodiments, the circle portion 18 may not have any $O_2$ sensor, and oxygen sensing may instead occur at the sampling port at the patient end of the patient connector 27.

In certain embodiments, the system may include a front housing piece 80 which is a superficial piece that incorporates with the housing of the anesthesia machine 1. In certain embodiments, the front housing piece 80 may be removable and reusable, where the inspiratory and expiratory ports 26 and 29 go through openings 81 and 82 in the housing and extend therefrom. In other embodiments, the front housing piece 80 may be an integrated part of the disposable circle portion 18.

In various embodiments, the $CO_2$ absorber 20 may be a disposable canister that is removably connected to the circle portion 18. As shown in FIG. 3C, the canister may be removably connected to the circle portion 18 by connection means. Specifically, connectors on the canister 85 may be configured to mate with reciprocal connectors 86 on the disposable circle portion 18. When connected, the absorber inlet and outlet ports 21', 22' align with reciprocal ports on the disposable circle portion 18. Thereby, the $CO_2$ absorber 20 can be removed and replaced, such as during a long case where the $CO_2$ absorber expires and a new one is needed. In other embodiments, the $CO_2$ absorber 20 may be an integrated part of the circle portion 18, and thus replacement of the $CO_2$ absorber 20 requires replacement of the entire disposable circle portion 18.

In various embodiments, the disposable circle portion 18 may be made of any material configured for disposal. For example, the circle portion 18 may be a molded plastic material. Since the disposable circle portion 18 does not need to be autoclaved or sterilized, the plastic material does not need to be autoclavable. For example, the disposable circle portion 18 shown in FIG. 3C may be provided as a single piece of molded plastic configured to connect to the disposable $CO_2$ absorber 20, such as injection molded polyethylene or polypropylene. In certain embodiments, the front housing piece 80 may be part of the molded disposable circle portion 18.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:
1. An anesthesia machine comprising:
  a gas mixer that receives gas from at least two gas sources and provides an anesthetic gas for delivery to a ventilated patient;
  a breathing system comprising:
    a reusable ventilation portion including a mechanical ventilation section, a manual ventilation section, a ventilation port, and a switch configured to switch between connection of the mechanical ventilation section to drive patient ventilation through the ventilation port and connection of the manual ventilation section to drive the patient ventilation through the ventilation port;

a disposable circle portion removably connected to the reusable ventilation portion, the disposable circle portion including:
- a vent connector that connects to the ventilation port;
- an inspiratory channel configured to conduct inspiratory gasses and terminating at an inspiratory port that connects to a patient connector and delivers the inspiratory gases thereto;
- a gas intake port providing anesthetic gas from the gas mixer to the inspiratory channel;
- an expiratory channel configured to conduct expiratory gasses and terminating at an expiratory port that connects to the patient connector and receives the expiratory gases therefrom;
- a CO2 absorber connecting between the expiratory channel and the inspiratory channel; and
- a filter positioned between the expiratory port and the vent connector and between the CO2 absorber and the vent connector, wherein the filter prevents moisture and bacteria from entering the reusable ventilation portion of the breathing system.

2. The anesthesia machine of claim 1, further comprising a common channel connecting between the vent connector, the expiratory channel, and the CO2 absorber, wherein the filter is in the common channel.

3. The anesthesia machine of claim 1, wherein the filter is integrated into the vent connector.

4. The anesthesia machine of claim 1, wherein the filter includes a heat and moisture exchange filter (HMEF).

5. The anesthesia machine of claim 1, wherein the filter includes a high efficiency particulate air (HEPA) filter.

6. The anesthesia machine of claim 1, wherein the CO2 absorber is a disposable canister that is removably connected to the disposable circle portion such that the CO2 absorber can be removed and replaced without removal of the disposable circle portion from the breathing system.

7. The anesthesia machine of claim 1, wherein the disposable circle portion is comprised of plastic and is configured for use with only a single patient.

8. The anesthesia machine of claim 1, wherein the breathing system is removable from and attachable to the anesthesia machine as a single piece.

9. The anesthesia machine of claim 8, wherein the disposable circle portion further comprises a first fitting configured to mate with a reciprocal fitting on the reusable ventilation portion so as to fasten the disposable circle portion of the breathing system to the reusable ventilation portion.

10. The anesthesia machine of claim 9, wherein the disposable circle portion is formed as a molded plastic configured for use with a single patient.

11. The anesthesia machine of claim 9, wherein the disposable circle portion further includes a one-way inspiratory valve and an inspiratory sensor in the inspiratory channel, and one-way expiratory valve and an expiratory sensor in the expiratory channel.

12. A breathing system for an anesthesia machine comprising:
- a reusable ventilation portion including a mechanical ventilation section, a manual ventilation section, a ventilation port, and a switch configured to switch between connection of the mechanical ventilation section to drive patient ventilation through the ventilation port and connection of the manual ventilation section to drive the patient ventilation through the ventilation port;
- a disposable circle portion removably connected to the reusable ventilation portion, the disposable circle portion including:
  - a vent connector that connects to the ventilation port;
  - an inspiratory channel configured to conduct inspiratory gasses and terminating at an inspiratory port that connects to a patient connector and delivers the inspiratory gases thereto;
  - a gas intake port providing anesthetic gas from a gas mixer to the inspiratory channel;
  - an expiratory channel configured to conduct expiratory gasses and terminating at an expiratory port that connects to the patient connector and receives the expiratory gases therefrom;
  - a CO2 absorber connecting between the expiratory channel and the inspiratory channel; and
  - a filter positioned in a flow path of the expiratory gases between the expiratory port and the vent connector, wherein the filter prevents moisture and bacteria in the expiratory gases from entering the reusable ventilation portion of the breathing system.

13. The breathing system of claim 12, wherein the filter is further positioned in a flow path between the CO2 absorber and the vent connector.

14. The breathing system of claim 13, further comprising a common channel connecting between the vent connector, the expiratory channel, and the CO2 absorber, wherein the filter is in the common channel.

15. The breathing system of claim 13, wherein the filter is integrated into the vent connector.

16. The breathing system of claim 12, wherein the CO2 absorber is a disposable canister that is removably connected to the disposable circle portion such that the CO2 absorber can be removed and replaced without removal of the disposable circle portion from the breathing system.

17. The breathing system of claim 12, wherein the filter includes at least one of a heat and moisture exchange filter (HMEF) and a high efficiency particulate air (HEPA) filter.

18. The breathing system of claim 12, wherein the disposable circle portion is comprised of molded plastic and is configured for use with only a single patient.

19. The breathing system of claim 12, wherein the disposable circle portion further includes a one-way inspiratory valve and an inspiratory sensor in the inspiratory channel, and one-way expiratory valve and an expiratory sensor in the expiratory channel.

20. The breathing system of claim 19, wherein the disposable circle portion further includes an O2 sensor in the inspiratory channel.

* * * * *